US009121067B2

(12) United States Patent
Delmar et al.

(10) Patent No.: US 9,121,067 B2
(45) Date of Patent: Sep. 1, 2015

(54) PREDICTIVE MARKER FOR EGFR INHIBITOR TREATMENT

(71) Applicant: Hoffmann-La Roche Inc., Nutley, NJ (US)

(72) Inventors: Paul Delmar, Basel (CH); Barbara Klughammer, Rheinfelden (DE); Verena Lutz, Bad Toelz (DE); Patricia McLoughlin, Newcastle (GB)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/854,180

(22) Filed: Apr. 1, 2013

(65) Prior Publication Data

US 2013/0210843 A1 Aug. 15, 2013

Related U.S. Application Data

(63) Continuation of application No. 12/672,959, filed as application No. PCT/EP2008/006523 on Aug. 7, 2008.

(30) Foreign Application Priority Data

Aug. 14, 2007 (EP) ..................................... 07114302

(51) Int. Cl.
*C12Q 1/68* (2006.01)
*C07H 21/04* (2006.01)
*A61K 31/517* (2006.01)

(52) U.S. Cl.
CPC ............. *C12Q 1/6886* (2013.01); *A61K 31/517* (2013.01); *C12Q 2600/106* (2013.01); *C12Q 2600/118* (2013.01); *C12Q 2600/158* (2013.01)

(58) Field of Classification Search
CPC .............. A61K 31/517; A61K 31/519; A61K 39/39558; A61K 2039/505; A61K 31/282; A61K 31/7072; A61K 31/506; A61K 31/555; A61K 31/704; A61K 31/365; A61K 31/395; A61K 31/78068; A61K 31/415; A61K 38/38; A61K 39/395; C12Q 1/6886; C12Q 2600/106; C12Q 2600/118; C12Q 2600/158; C12Q 1/6896; C12Q 2531/113; C12Q 2537/143; C12Q 2537/149; C12Q 1/6858; C12Q 1/686; C12Q 1/68; C12Q 1/6844; C12Q 1/6851; C12Q 1/6881; C12Q 1/6883; C12Q 2600/156; C12Q 2600/112; C12Q 2600/136; C12Q 2600/178; C12Q 21/6806; C12Q 1/6809; C12Q 1/6813; C12Q 1/6837
See application file for complete search history.

(56) References Cited

U.S. PATENT DOCUMENTS

| | | | |
|---|---|---|---|
| 5,202,231 A | 4/1993 | Drmanac et al. | |
| 5,445,934 A | 8/1995 | Fodor et al. | |
| 5,525,464 A | 6/1996 | Drmanac et al. | |
| 5,695,940 A | 12/1997 | Drmanac et al. | |
| 5,744,305 A | 4/1998 | Fodor et al. | |
| 5,795,716 A | 8/1998 | Chee et al. | |
| 5,800,992 A | 9/1998 | Fodor et al. | |
| 2006/0234237 A1* | 10/2006 | Amler et al. | 435/6 |
| 2006/0252056 A1* | 11/2006 | Tsuruo et al. | 435/6 |

FOREIGN PATENT DOCUMENTS

| | | |
|---|---|---|
| WO | 2004/111273 A2 | 12/2004 |
| WO | 2004/111273 A3 | 12/2004 |
| WO | 2005/049829 A1 | 6/2005 |

OTHER PUBLICATIONS

Peterson, RP et al. Journal of Clinical Oncology 2005 Vol 23 No. 16S p. 7020.*
Whitehead, Andrew et al. Variation in tissue specific gene expression among natural populations. Genome Biology 2005 vol. 6 Issue 2 Article R13.*
Roman-Roman, Set al. Identification of genes regulated during osteoblastic differentiation by genome wide expression analysis of mouse calvaria primary osteoblasts in vitro. Bone 2003 vol. 32 pp. 474-482.*
Hoshikawa, Yasushit et al. Hypoxia induces different genes in the lungs of rats compared with mice. Physical Genomics 2003 Vol 12 pp. 209-219.*
Chan, Eric. Integrating Transcriptomics and Proteomics. G&P magazine 2006 vol. 6 No. 3 pp. 20-26.*
Evans, William et al. Moving towards individualized medicine with pharmacogenomics. Nature 2004. vol. 429, pp. 464-468.*
(Translation of Chinese Off Act in Corres Chines Appl 200880102703.8 Nov. 1, 2012).
(Translation of Israeli Off Act in Corres Israeli App 203647 Jan. 25, 2012).
(Translation of Jap Off Act in Corres Jap App 2010520472 Aug. 28, 2012).
Coldren C D et al., "Baseline Gene Expression PRedicts Sensitivity to Gefitinib in Non-SMall Cell Lung Cancer Cell Lines" Molecular Cancer Research 4(8):521-528 (Aug. 2006)
Gridelli et al., "Erlotinib in non-small cell lung cancer treatment: current status and future development" ONCOLOGIST 12(7):840-849 (2007).
Iyer et al., "The Transcriptional program in the response of human fibroblast to serum" SCIENCE 283:83-87 (Jan. 1, 1991).
Johnston et al., "Gene Chips: Array of hope for understnading gene regulation" CURR BIOL 8:R171-R174 (1998).
Kakiuchi, Soji et al., "Prediction of sensitivity of advanced non-small cell lung cancers to gefitinib" Human Molecular Genetics 13(24):3029-3043 (Oct. 20, 2004).
Kokubo et al., "Reduction of PTEN protein and loss of epidermal growth factor receptor gene mutation in lung cancer with natural resistance of gefitinib" BR J CANCER 92(9):1711-1719 (2005).

(Continued)

*Primary Examiner* — Amanda Haney
(74) *Attorney, Agent, or Firm* — Jones Day

(57) ABSTRACT

The present invention provides a biomarker which is predictive for the clinical benefit of EGFR inhibitor treatment in cancer patients.

1 Claim, 3 Drawing Sheets

(56) References Cited

OTHER PUBLICATIONS

Okano et al., "Proteomic signature corresponding to the response to gefitinib, an epidermal growth factor receptor tyrosine kinase inhibitor in lung adenocarcinoma" CLIN CANCER RES 13(3):799-805 (Feb. 1, 2007).

retreived on Aug. 17, 2012 from the Internet: URL:http://www.ncbi.nlm.nih.gov/geo/query/acc.cgi?acc=GPL96 (Affimetrix Human Genome U13A Array uploaded Mar. 11, 2002).

Zhou et al., "Targeting ADAM-mediated ligand cleavage to invibit HER3 and EGFR pathways in non-small cell lung cancer" CANCER CELL 10(1):39-50 (Jul. 2006).

* cited by examiner

PREDICTIVE MARKER FOR EGFR INHIBITOR TREATMENT

PRIORITY TO RELATED APPLICATIONS

This application is a continuation of application Ser. No. 12/672,959 filed Feb. 10, 2010 which is the National Stage of International Application No. PCT/EP2008/006523, filed Aug. 7, 2008, which claims the benefit of EP 07114302.8 filed Aug. 14, 2007, which is hereby incorporated by reference in its entirety.

The present invention provides a biomarker that is predictive for the clinical benefit of EGFR inhibitor treatment in cancer patients.

A number of human malignancies are associated with aberrant or over-expression of the epidermal growth factor receptor (EGFR). EGF, transforming growth factor-? (TGF-?), and a number of other ligands bind to the EGFR, stimulating autophosphorylation of the intracellular tyrosine kinase domain of the receptor. A variety of intracellular pathways are subsequently activated, and these downstream events result in tumour cell proliferation in vitro. It has been postulated that stimulation of tumour cells via the EGFR may be important for both tumour growth and tumour survival in vivo.

Early clinical data with Tarceva™, an inhibitor of the EGFR tyrosine kinase, indicate that the compound is safe and generally well tolerated at doses that provide the targeted effective concentration (as determined by preclinical data). Clinical phase I and II trials in patients with advanced disease have demonstrated that Tarceva™ has promising clinical activity in a range of epithelial tumours. Indeed, Tarceva™ has been shown to be capable of inducing durable partial remissions in previously treated patients with head and neck cancer, and NSCLC (Non small cell lung cancer) of a similar order to established second line chemotherapy, but with the added benefit of a better safety profile than chemo therapy and improved convenience (tablet instead of intravenous [i.v.] administration). A recently completed, randomised, double-blind, placebo-controlled trial (BR.21) has shown that single agent Tarceva™ significantly prolongs and improves the survival of NSCLC patients for whom standard therapy for advanced disease has failed.

Tarceva™ (erlotinib) is a small chemical molecule; it is an orally active, potent, selective inhibitor of the EGFR tyrosine kinase (EGFR-TKI).

Lung cancer is the major cause of cancer-related death in North America and Europe. In the United States, the number of deaths secondary to lung cancer exceeds the combined total deaths from the second (colon), third (breast), and fourth (prostate) leading causes of cancer deaths combined. About 75% to 80% of all lung cancers are NSCLC, with approximately 40% of patients presenting with locally advanced and/or unresectable disease. This group typically includes those with bulky stage IIIA and IIIB disease, excluding malignant pleural effusions.

The crude incidence of lung cancer in the European Union is 52.5, the death rate 48.7 cases/100000/year. Among men the rates are 79.3 and 78.3, among women 21.6 and 20.5, respectively. NSCLC accounts for 80% of all lung cancer cases. About 90% of lung cancer mortality among men, and 80% among women, is attributable to smoking.

In the US, according to the American Cancer Society, during 2004, there were approximately 173,800 new cases of lung cancer (93,100 in men and 80,700 in women) and were accounting for about 13% of all new cancers. Most patients die as a consequence of their disease within two years of diagnosis. For many NSCLC patients, successful treatment remains elusive. Advanced tumours often are not amenable to surgery and may also be resistant to tolerable doses of radiotherapy and chemotherapy. In randomized trials the currently most active combination chemotherapies achieved response rates of approximately 30% to 40% and a 1-year survival rate between 35% and 40%. This is really an advance over the 10% 1-year survival rate seen with supportive care alone.

Until recently therapeutic options for relapsed patients following relapse were limited to best supportive care or palliation. A recent trial comparing docetaxel (Taxotere) with best supportive care showed that patients with NSCLC could benefit from second line chemotherapy after cisplatin-based first-line regimens had failed. Patients of all ages and with ECOG performance status of 0, 1, or 2 demonstrated improved survival with docetaxel, as did those who had been refractory to prior platinum-based treatment. Patients who did not benefit from therapy included those with weight loss of 10%, high lactate dehydrogenase levels, multi-organ involvement, or liver involvement. Additionally, the benefit of docetaxel monotherapy did not extend beyond the second line setting. Patients receiving docetaxel as third-line treatment or beyond showed no prolongation of survival. Single-agent docetaxel became a standard second-line therapy for NSCLC. Recently another randomized phase III trial in second line therapy of NSCLC compared pemetrexed (Alimta®) with docetaxel. Treatment with pemetrexed resulted in a clinically equivalent efficacy but with significantly fewer side effects compared with docetaxel.

It has long been acknowledged that there is a need to develop methods of individualising cancer treatment. With the development of targeted cancer treatments, there is a particular interest in methodologies which could provide a molecular profile of the tumour target, (i.e. those that are predictive for clinical benefit). Proof of principle for gene expression profiling in cancer has already been established with the molecular classification of tumour types which are not apparent on the basis of current morphological and immunohistochemical tests. Two separate disease entities were differentiated with differing prognoses from the single current classification of diffuse large B-cell lymphoma using gene expression profiling.

Therefore, it is an aim of the present invention to provide expression biomarkers that are predictive for the clinical benefit of EGFR inhibitor treatment in cancer patients.

In a first object the present invention provides an in vitro method of predicting the clinical benefit of a cancer patient in response to treatment with an EGFR inhibitor comprising the steps: determining an expression level of a PTPRF gene in a tumour sample of a patient and comparing the expression level of the PTPRF gene to a value representative of an expression level of the PTPRF gene in tumours of a population of patients deriving no clinical benefit from the treatment, wherein a higher expression level of the PTPRF gene in the tumour sample of the patient is indicative for a patient who will derive clinical benefit from the treatment.

The abbreviation PTPRF means protein tyrosine phosphatase, receptor type, F. Seq. Id. No. 1 shows the nucleotide sequence of human PTPRF, transcript variant 1 and Seq. Id. No. 2 shows the nucleotide sequence of human PTPRF transcript variant 2.

The term "a value representative of an expression level of PTPRF in tumours of a population of patients deriving no clinical benefit from the treatment" refers to an estimate of the mean expression level of the PTPRF gene in a population of patients who do not derive a clinical benefit from the treatment. Clinical benefit was defined as either having an objective response or disease stabilization for ≥12 weeks.

In a further preferred embodiment, the PTPRF gene shows between 1.1 and 1.8, preferably 1.1 and 1.6, or more fold higher expression level in the tumour sample of the patient compared to a value representative of the population of patients deriving no clinical benefit from the treatment.

In a further preferred embodiment, the PTPRF gene shows between 1.2 and 1.8 or more fold higher expression level in the tumour sample of the patient compared to a value representative of the population of patients deriving no clinical benefit from the treatment.

In a preferred embodiment, the expression level of the marker gene is determined by microarray technology or other technologies that assess RNA expression levels like quantitative RT-PCR, or by any method looking at the expression level of the respective protein, eg immunohistochemistry (IHC). The construction and use of gene chips are well known in the art. see, U.S. Pat. Nos. 5,202,231; 5,445,934; 5,525,464; 5,695,940; 5,744,305; 5,795,716 and 1 5,800,992. See also, Johnston, M. Curr. Biol. 8:R171-174 (1998); Iyer V R et al., Science 283:83-87 (1999). Of course, the gene expression level can be determined by other methods that are known to a person skilled in the art such as e.g. northern blots, RT-PCR, real time quantitative PCR, primer extension, RNase protection, RNA expression profiling.

The marker gene of the present invention can be combined with other biomarkers to biomarker sets. Biomarker sets can be built from any combination of predictive biomarkers to make predictions about the effect of EGFR inhibitor treatment in cancer patients. The biomarkers and biomarkers sets described herein can be used, for example, to predict how patients with cancer will respond to therapeutic intervention with an EGFR inhibitor.

The term "gene" as used herein comprises variants of the gene. The term "variant" relates to nucleic acid sequences which are substantially similar to the nucleic acid sequences given by the GenBank accession number. The term "substantially similar" is well understood by a person skilled in the art. In particular, a gene variant may be an allele which shows nucleotide exchanges compared to the nucleic acid sequence of the most prevalent allele in the human population. Preferably, such a substantially similar nucleic acid sequence has a sequence similarity to the most prevalent allele of at least 80%, preferably at least 85%, more preferably at least 90%, most preferably at least 95%. The term "variants" is also meant to relate to splice variants.

The EGFR inhibitor can be selected from the group consisting of gefitinib, erlotinib, PKI-166, EKB-569, GW2016, CI-1033 and an anti-erbB antibody such as trastuzumab and cetuximab.

In another embodiment, the EGFR inhibitor is erlotinib.

In yet another embodiment, the cancer is NSCLC.

Techniques for the detection and quantification of gene expression of the genes described by this invention include, but are not limited to northern blots, RT-PCR, real time quantitative PCR, primer extension, RNase protection, RNA expression profiling and related techniques. These techniques are well known to those of skill in the art see e.g. Sambrook J et al., Molecular Cloning: A Laboratory Manual, Third Edition (Cold Spring Harbor Press, Cold Spring Harbor, 2000).

Techniques for the detection of protein expression of the respective genes described by this invention include, but are not limited to immunohistochemistry (IHC).

In accordance with the invention, cells from a patient tissue sample, e.g., a tumour or cancer biopsy, can be assayed to determine the expression pattern of one or more biomarkers. Success or failure of a cancer treatment can be determined based on the biomarker expression pattern of the cells from the test tissue (test cells), e.g., tumour or cancer biopsy, as being relatively similar or different from the expression pattern of a control set of the one or more biomarkers. In the context of this invention, it was found that the gene of table 3 is up regulated i.e. shows a higher expression level, in tumours of patients who derived clinical benefit from EGFR inhibitor treatment compared to tumours of patients who did not derive clinical benefit from the EGFR inhibitor treatment. Thus, if the test cells show a biomarker expression profile which corresponds to that of a patient who responded to cancer treatment, it is highly likely or predicted that the individual's cancer or tumour will respond favorably to treatment with the EGFR inhibitor. By contrast, if the test cells show a biomarker expression pattern corresponding to that of a patient who did not respond to cancer treatment, it is highly likely or predicted that the individual's cancer or tumour will not respond to treatment with the EGFR inhibitor.

The biomarker of the present invention i.e. the gene listed in table 3, is a first step towards an individualized therapy for patients with cancer, in particular patients with refractory NSCLC. This individualized therapy will allow treating physicians to select the most appropriate agent out of the existing drugs for cancer therapy, in particular NSCLC. The benefit of individualized therapy for each future patient are: response rates/number of benefiting patients will increase and the risk of adverse side effects due to ineffective treatment will be reduced.

In a further object the present invention provides a therapeutic method of treating a cancer patient identified by the in vitro method of the present invention. Said therapeutic method comprises administering an EGFR inhibitor to the patient who has been selected for treatment based on the predictive expression pattern of the gene of table 3. A preferred EGFR inhibitor is erlotinib and a preferred cancer to be treated is NSCLC.

SHORT DESCRIPTION OF THE FIGURES

EXPERIMENTAL PART

Figure 1:
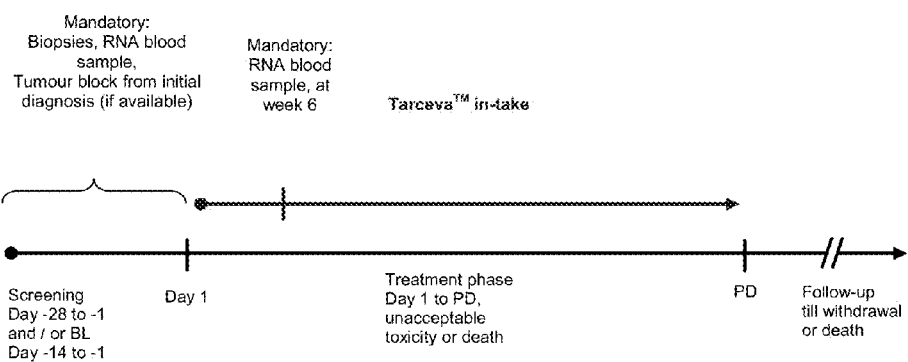
FIG. 1 shows the study design.

Rationale for the Study and Study Design

Recently mutations within the EGFR gene in the tumour tissue of a subset of NSCLC patients and the association of these mutations with sensitivity to erlotinib and gefitinib were described (Pao W, et al. 2004; Lynch et al. 2004; Paez et al. 2004). For the patients combined from two studies, mutated EGFR was observed in 13 of 14 patients who responded to gefitinib and in none of the 11 gefitinib-treated patients who did not respond. The reported prevalence of these mutations was 8% (2 of 25) in unselected NSCLC patients. These mutations were found more frequently in adenocarcinomas (21%), in tumours from females (20%), and in tumours from Japanese patients (26%). These mutations result in increased in vitro activity of EGFR and increased sensitivity to gefitinib. The relationship of the mutations to prolonged stable disease or survival duration has not been prospectively evaluated.

Based on exploratory analyses from the BR.21 study, it appeared unlikely that the observed survival benefit is only due to the EGFR mutations, since a significant survival benefit is maintained even when patients with objective response are excluded from analyses (data on file). Other molecular mechanisms must also contribute to the effect.

Based on the assumption that there are changes in gene expression levels that are predictive of response/benefit to Tarceva™ treatment, microarray analysis was used to detect these changes\

This required a clearly defined study population treated with Tarceva™ monotherapy after failure of 1st line therapy. Based on the experience from the BR.21 study, benefiting population was defined as either having objective response, or disease stabilization for 12 weeks. Clinical and microarray datasets were analyzed according to a pre-defined statistical plan.

The application of this technique requires fresh frozen tissue (FFT). Therefore a mandatory biopsy had to be performed before start of treatment. The collected material was frozen in liquid nitrogen (N2).

A second tumour sample was collected at the same time and stored in paraffin (formalin fixed paraffin embedded, FFPE). This sample was analysed for alterations in the EGFR signaling pathway.

The ability to perform tumour biopsies via bronchoscopy was a prerequisite for this study. Bronchoscopy is a standard procedure to confirm the diagnosis of lung cancer. Although generally safe, there is a remaining risk of complications, e.g. bleeding.

This study was a first step towards an individualized therapy for patients with refractory NSCLC. This individualized therapy will allow treating physicians to select the most appropriate agent out of the existing drugs for this indication.

Once individualized therapy will be available, the benefit for each future patient will outweigh the risk patients have to take in the present study:

response rates/number of benefiting patients will increase, the risk of adverse side effects due to ineffective treatment will be reduced.

Rationale for Dosage Selection

Tarceva™ was given orally once per day at a dose of 150 mg until disease progression, intolerable toxicities or death. The selection of this dose was based on pharmacokinetic parameters, as well as the safety and tolerability profile of this dose observed in Phase I, II and III trials in heavily pre-treated patients with advanced cancer. Drug levels seen in the plasma of patients with cancer receiving the 150 mg/day dose were consistently above the average plasma concentration of 500 ng/ml targeted for clinical efficacy. BR.21 showed a survival benefit with this dose.

Objectives of the Study

The primary objective was the identification of differentially expressed genes that are predictive for benefit (CR, PR or SD ? 12 weeks) of Tarceva™ treatment. Identification of differentially expressed genes predictive for "response" (CR, PR) to Tarceva™ treatment was an important additional objective.

The secondary objectives were to assess alterations in the EGFR signaling pathways with respect to benefit from treatment.

Study Design

Overview of Study Design and Dosing Regimen

This was an open-label, predictive marker identification Phase II study. The study was conducted in approximately 26 sites in about 12 countries. 264 patients with advanced NSCLC following failure of at least one prior chemotherapy regimen were enrolled over a 12 month period. Continuous oral Tarceva™ was given at a dose of 150 mg/day. Dose reductions were permitted based on tolerability to drug therapy. Clinical and laboratory parameters were assessed to evaluate disease control and toxicity. Treatment continued until disease progression, unacceptable toxicity or death. The study design is depicted in FIG. 1.

Tumour tissue and blood samples were obtained for molecular analyses to evaluate the effects of Tarceva™ and to identify subgroups of patients benefiting from therapy.

Predictive Marker Assessments

Biopsies of the tumour were taken within 2 weeks before start of treatment. Two different samples were collected:

The first sample was always frozen immediately in liquid N2

The second sample was fixed in formalin and embedded in paraffin\

Snap frozen tissue had the highest priority in this study.

Figure 2:
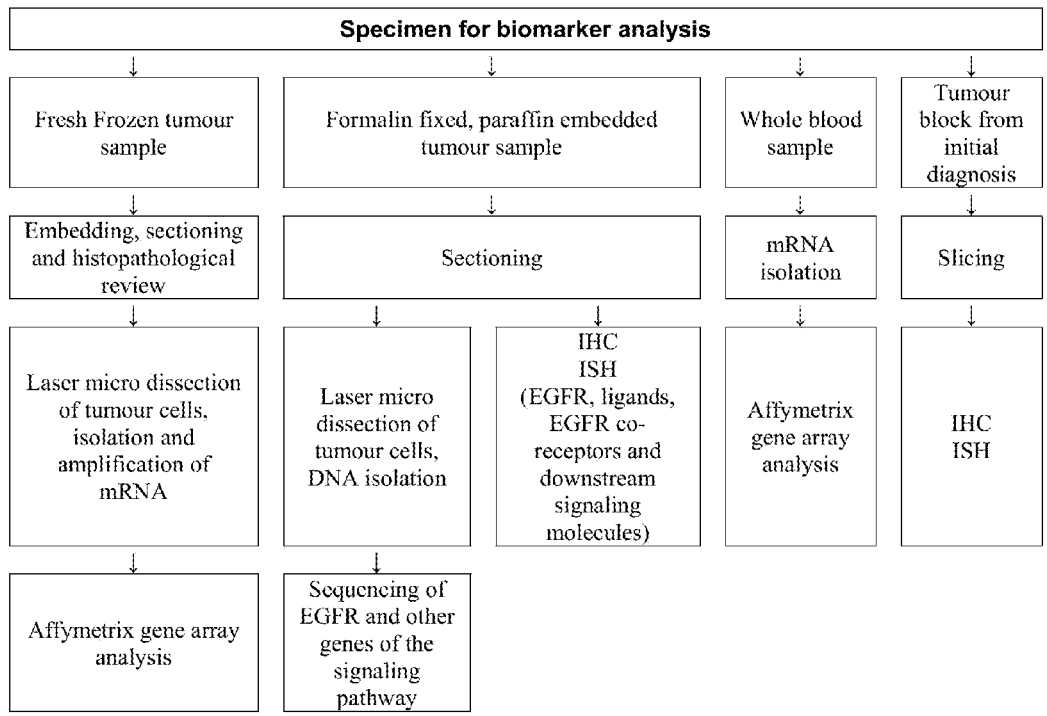
FIG. 2 shows the scheme of sample processing.

FIG. 2 shows a scheme of the sample processing.

Microarray Analysis

The snap frozen samples were used for laser capture microdissection (LCM) of tumour cells to extract tumour RNA and RNA from tumour surrounding tissue. The RNA was analysed on Affymetrix microarray chips (HG-U133A) to establish the patients' tumour gene expression profile. Quality Control of Affymetrix chips was used to select those samples of adequate quality for statistical comparison.

Single Biomarker Analyses on Formalin Fixed Paraffin Embedded Tissue

The second tumour biopsy, the FFPE sample, was used to perform DNA mutation, IHC and ISH analyses as described below. Similar analyses were performed on tissue collected at initial diagnosis.

The DNA mutation status of the genes encoding EGFR and other molecules involved in the EGFR signaling pathway were analysed by DNA sequencing. Gene amplification of EGFR and related genes were be studied by FISH.

Protein expression analyses included immunohistochemical [IHC] analyses of EGFR and other proteins within the EGFR signalling pathway.

Response Assessments

The RECIST (Uni-dimensional Tumour Measurement) criteria were used to evaluate response.

Note that:

To be assigned a status of CR or PR, changes in tumour measurements must be confirmed by repeated assessments at least 4 weeks apart at any time during the treatment period.

In the case of SD, follow-up measurements must have met the SD criteria at least once after study entry at a minimum interval of 6 weeks.

In the case of maintained SD, follow-up measurements must have met the SD criteria at least once after study entry with maintenance duration of at least 12 weeks.

Survival Assessment

A regular status check every 3 months was performed either by a patient's visit to the clinic or by telephone. All deaths were recorded. At the end of the study a definitive confirmation of survival was required for each patient.

Methods

RNA Sample Preparation and Quality Control of RNA Samples

All biopsy sample processing was handled by a pathology reference laboratory; fresh frozen tissue samples were shipped from investigator sites to the Clinical Sample Operations facility in Roche Basel and from there to the pathology laboratory for further processing. Laser capture microdissection was used to select tumour cells from surrounding tissue. After LCM, RNA was purified from the enriched tumour material. The pathology laboratory then carried out a number of steps to make an estimate of the concentration and quality of the RNA.

RNases are RNA degrading enzymes and are found everywhere and so all procedures where RNA will be used must be strictly controlled to minimize RNA degradation. Most mRNA species themselves have rather short half-lives and so are considered quite unstable. Therefore it is important to perform RNA integrity checks and quantification before any assay.

RNA concentration and quality profile can be assessed using an instrument from Agilent (Agilent Technologies, Inc., Palo Alto, Calif.) called a 2100 Bioanalyzer®. The instrument software generates an RNA Integrity Number (RIN), a quantitation estimate (Schroeder, A., et al., The RIN: an RNA integrity number for assigning integrity values to RNA measurements. BMC Mol Biol, 2006. 7: p. 3), and calculates ribosomal ratios of the total RNA sample. The RIN is determined from the entire electrophoretic trace of the RNA sample, and so includes the presence or absence of degradation products.

The RNA quality was analysed by a 2100 Bioanalyzer®. Only samples with at least one rRNA peak above the added poly-I noise and sufficient RNA were selected for further analysis on the Affymetrix platform. The purified RNA was forwarded to the Roche Centre for Medical Genomics (RCMG; Basel, Switzerland) for analysis by microarray. 122 RNA samples were received from the pathology lab for further processing.

Target Labeling of Tissue RNA Samples

Target labeling was carried out according to the Two-Cycle Target Labeling Amplification Protocol from Affymetrix (Affymetrix, Santa Clara, Calif.), as per the manufacturer's instructions.

The method is based on the standard Eberwine linear amplification procedure but uses two cycles of this procedure to generate sufficient labeled cRNA for hybridization to a microarray.

Total RNA input used in the labeling reaction was 10 ng for those samples where more than 10 ng RNA was available; if less than this amount was available or if there was no quantity data available (due to very low RNA concentration), half of the total sample was used in the reaction. Yields from the labeling reactions ranged from 20-180 μg cRNA. A normalization step was introduced at the level of hybridization where 15 μg cRNA was used for every sample.

Human Reference RNA (Stratagene, Carlsbad, Calif., USA) was used as a control sample in the workflow with each batch of samples. 10 ng of this RNA was used as input alongside the test samples to verify that the labeling and hybridization reagents were working as expected.

Microarray Hybridizations

Affymetrix HG-U133A microarrays contain over 22,000 probe sets targeting approximately 18,400 transcripts and variants which represent about 14,500 well-characterized genes.

Hybridization for all samples was carried out according to Affymetrix instructions (Affymetrix Inc., Expression Analysis Technical Manual, 2004). Briefly, for each sample, 15 μg of biotin-labeled cRNA were fragmented in the presence of divalent cations and heat and hybridized overnight to Affymetrix HG-U133A full genome oligonucleotide arrays. The following day arrays were stained with streptavidin-phycoerythrin (Molecular Probes; Eugene, Oreg.) according to the manufacturer's instructions. Arrays were then scanned using a GeneChip Scanner 3000 (Affymetrix), and signal intensities were automatically calculated by GeneChip Operating Software (GCOS) Version 1.4 (Affymetrix).

Statistical Analysis

Analysis of the Affymetrix™ data consisted of five main steps.

Step 1 was quality control. The goal was to identify and exclude from analysis array data with a sub-standard quality profile.

Step 2 was pre-processing and normalization. The goal was to create a normalized and scaled "analysis data set", amenable to inter-chip comparison. It comprised background noise estimation and subtraction, probe summarization and scaling.

Step 3 was exploration and description. The goal was to identify potential bias and sources of variability. It consisted of applying multivariate and univariate descriptive analysis techniques to identify influential covariates.

Step 4 was modeling and testing. The goal was to identify a list of candidate markers based on statistical evaluation of the difference in mean expression level between "clinical benefit" and "no clinical benefit" patients. It consisted in fitting an adequate statistical model to each probe-set and deriving a measure of statistical significance.

Step 5 was a robustness analysis. The goal was to generate a qualified list of candidate markers that do not heavily depend on the pre-processing methods and statistical assumptions. It consisted in reiterating the analysis with different methodological approaches and intersecting the list of candidates.

All analyses were performed using the R software package.

Step 1: Quality Control

The assessment of data quality was based on checking several parameters. These included standard Affymetrix GeneChip™ quality parameters, in particular: Scaling Factor, Percentage of Present Call and Average Background. This step also included visual inspection of virtual chip images for detecting localized hybridization problems, and comparison of each chip to a virtual median chip for detecting any unusual departure from median behaviour. Inter-chip correlation analysis was also performed to detect outlier samples. In addition, ancillary measures of RNA quality obtained from analysis of RNA samples with the Agilent Bioanalyzer™ 2100 were taken into consideration.

Based on these parameters, data from 20 arrays were excluded from analysis. Thus data from a total of 102 arrays representing 102 patients was included in the analysis. The clinical description of these 102 samples set is reported in table 1.

TABLE 1

Description of clinical characteristics of patients included in the analysis

| Variable | Value | n = 102<br>n (%) |
|---|---|---|
| Best Response | N/A | 16 (15.7%) |
|  | PD | 49 (48.0%) |
|  | SD | 31 (30.4%) |
|  | PR | 6 (5.9%) |
| Clinical Benefit | NO | 81 (79.4%) |
|  | YES | 21 (20.6%) |
| SEX | FEMALE | 25 (24.5%) |
|  | MALE | 77 (74.5%) |
| ETHNICITY | CAUCASIAN | 65 (63.7%) |
|  | ORIENTAL | 37 (36.3%) |
| Histology | ADENOCARCINOMA | 35 (34.3%) |
|  | SQUAMOUS | 53 (52.0%) |
|  | OTHERS | 14 (13.7%) |

TABLE 1-continued

Description of clinical characteristics of patients included in the analysis

| Variable | Value | n = 102 n (%) |
|---|---|---|
| Ever-Smoking | NO | 20 (19.6%) |
|  | YES | 82 (80.4%) |

Step 2: Data Pre-Processing and Normalization

The rma algorithm (Irizarry, R. A., et al., Summaries of Affymetrix GeneChip probe level data. Nucl. Acids Res., 2003. 31(4): p. e15) was used for pre-processing and normalization. The mas5 algorithm (AFFYMETRIX, GeneChip® Expression: Data Analysis Fundamentals. 2004, AFFYMETRIX) was used to make detection calls for the individual probe-sets. Probe-sets called "absent" or "marginal" in all samples were removed from further analysis; 5930 probe-sets were removed from analysis based on this criterion. The analysis data set therefore consisted of a matrix with 16353 (out of 22283) probe-sets measured in 102 patients.

Step 3: Data Description and Exploration

Descriptive exploratory analysis was performed to identify potential bias and major sources of variability. A set of covariates with a potential impact on gene expression profiles was screened. It comprised both technical and clinical variables. Technical covariates included: date of RNA processing (later referred to as batch), RIN (as a measure of RNA quality/integrity), Operator and Center of sample collection. Clinical covariates included: Histology type, smoking status, tumour grade, performance score (Oken, M. M., et al., Toxicity and response criteria of the Eastern Cooperative Oncology Group. Am J Clin Oncol, 1982. 5(6): p. 649-55), demographic data, responder status and clinical benefit status.

The analysis tools included univariate ANOVA and principal component analysis. For each of these covariates, univariate ANOVA was applied independently to each probe-set.

A significant effect of the batch variable was identified. In practice, the batch variable captured differences between dates of sample processing and Affymetrix chip lot. After checking that the batch variable was nearly independent from the variables of interest, the batch effect was corrected using the method described in Johnson, W. E., C. Li, and A. Rabinovic, Adjusting batch effects in microarray expression data using empirical Bayes methods. Biostat, 2007. 8(1): p. 118-127.

The normalized data set after batch effect correction served as the analysis data set in subsequent analyses.

Histology and RIN were two additional important variables highlighted by the descriptive analysis.

Step 4: Data Modeling and testing.

A linear model was fitted independently to each probe-set. Variables included in the model are reported in table 2. The model parameters were estimated by the maximum likelihood technique. The parameter corresponding to the "Clinical Benefit" variable (XI) was used to assess the difference in expression level between the group of patients with clinical benefit and the group with no clinical benefit.

TABLE 2

Description of the variables included in the linear model.

| Variable | Type | Value |
|---|---|---|
| gene expression | Dependent ($Y_{ip}$) | log2 intensity of probe-set i in patient p. |
| Intercept | Overall mean ($\mu$) |  |
| Clinical Benefit | Predictor of interest (X1) | YES/NO |
| Histology | Adjustment Covariate (X2) | ADENO./SQUAM./OTHERS |
| RACE | Adj. Cov. (X3) | ORIENT./CAUCAS. |
| SEX | Adj. Cov. (X4) | FEMALE/MALE |
| RIN | Adj. Cov. (X5) | [2, . . . , 7.9] |
| SMOKER | Adj. Cov. (X6) | CURRENT/PAST/NEVER |
| Stage | Adj. Cov. (X7) | UNRESECT.III/IV |

For each probe-set i, the aim of the statistical test was to reject the hypothesis that the mean expression levels in patients with clinical benefit and patients without clinical benefit are equal, taking into account the other adjustment covariates listed in table 2. Formally, the null hypothesis of equality was tested against a two sided alternative. Under the null hypothesis, the distribution of the t-statistic for this test follows a Student t distribution with 92 degrees of freedom. The corresponding p-values are reported in table 3.

The choice of linear model was motivated by two reasons. Firstly, linear modeling is a versatile, well-characterized and robust approach that allows for adjustment of confounding variables when estimating the effect of the variable of interest. Secondly, given the sample size of 102, and the normalization and scaling of the data set, the normal distribution assumption was reasonable and justified.

For each probe-set, the assumption of homogeneity of variance was evaluated using Fligner-Killeen tests based on the model residuals. The analysis consisted of 3 steps:

1. Test each categorical variables for homogeneity of residual variance
2. Note the variable V with the least p-value
3. If the least p-value is less than 0.001, re-fit the model allowing the different level of variables V to have a different variance.

Step 5: Robustness

The goal of the robustness analysis was to reduce the risk that the results of the analysis might be artifactual and a result of the pre-processing steps or assumptions underlying the statistical analysis. The following three aspects were considered: a) inclusion or exclusion of a few extra chips at the quality control step; b) pre-processing and normalization algorithm; c) statistical assumptions and testing approach.

The list of candidate markers was defined as the subset of genes consistently declared as significant with different analysis settings. The different applied analysis options were the following:

a) An additional subset of 8 chips was identified based on more stringent quality control criteria. A "reduced data set" was defined by excluding these 8 chips.
b) MAS5 was identified as an alternative to rma for pre-processing and normalization. MAS5 uses different methods for background estimation, probe summarization and normalization.
c) Two additional statistical tests were employed.
   a. A wilcoxon test for the difference between clinical and no clinical benefit and
   b. a likelihood ratio test (LRT) testing for the logistic regression model where clinical benefit was taken as the response variable and gene expression as covariate. These two additional tests rely on a different set of underlying statistical assumptions. For each probe-set, the LRT was following a Chi-square with 1 degree of freedom.

In summary, two sets of samples (the "full" data-set and the "reduced" data-set), and 2 pre-processing algorithm (mas5 and rma) were considered; this resulted in four different analysis data sets. To each of these four data sets, three different statistical tests were applied. Therefore, for each probe-set, three p-values were calculated. In each analysis data set, a composite criterion was applied to identify the list of differentially regulated genes. This composite criterion was defined as: the maximum p-value is less than 0.05 and the minimum p-values is less than 0.001. The robustness analysis using criterion 1 for identifying marker genes yielded PTPRF as predictive marker for EGFR inhibitor treatment.

TABLE 3

Gene marker for Clinical Benefit based on the robustness analysis after application of the composite Criterion.

| Affymetrix Probe Set ID | GenBank | Gene | Adjusted Mean Fold Change | P-value | CI 95% |
|---|---|---|---|---|---|
| 200637_s_at | NM_002840 (Seq. Id. No. 1) NM_130440 (Seq. Id. No. 2) | PTPRF | 1.35 | 1.2E−3 | 1.1, 1.6 |
| 200635_s_at | NM_002840 (Seq. Id. No. 1) NM_130440 (Seq. Id. No. 2) | PTPRF | 1.49 | 1.7E−4 | 1.2, 1.8 |

Column 1 is the Affymetrix identifier of the probe-set.
Column 2 is the GenBank accession number of the corresponding gene sequence.
Column 3 is the corresponding official gene name.
Column 4 is the corresponding adjusted mean fold change in expression level between clinical and no clinical benefit patient, as estimated from the linear model.
Column 5 is the p-value for the test of difference in expression level between clinical benefit and no clinical benefit patients as derived from the linear model.
Column 6 is the 95% confidence interval for the adjusted mean fold change in expression level.

Further Statistical Analysis

For the selected candidate marker PTPRF, the following additional analyses were performed in a validated environment by an independent statisticians:

Univariate Cox Regression for PFS (Progression free survival) from Primary Affymetrix Analysis, Univariate Logistic Regression for Clinical Benefit from Primary Affymetrix Analysis, and Univariate Cox Regression for Survival from Primary Affymetrix Analysis The results of these analysis are presented below. They are consistent with the results of the primary analysis and confirm the choice of the selected marker.

Results: Univariate Cox Regression for PFS (Progression Free Survival) from Primary Affymetrix Analysis:

| Gene | No. of patients | Hazard ratio | 95% CI for Hazard ratio | p-Value |
|---|---|---|---|---|
| PTPRF | 102 | 0.5 | 0.34; 0.73 | 0.004 |

Results: Univariate Cox Regression for Clinical benefit from Primary Affymetrix Analysis:

| Gene | No. of patients | Odds ratio | 95% CI for Odds ratio | p-Value |
|---|---|---|---|---|
| PTPRF | 102 | 5.01 | 1.89; 13.33 | 0.0012 |

Results: Univariate Cox Regression for Survival from Primary Affymetrix Analysis:

| Gene | No. of patients | Hazard ratio | 95% CI for Hazard ratio | p-Value |
|---|---|---|---|---|
| PTPRF | 102 | 0.62 | 0.39; 0.97 | 0.0377 | qRT-PCR cDNA was synthesized using SuperScript™ III First-strand Synthesis SuperMix for qRT-PCR (Invitrogen, Calif., USA) according to the manufacturer's instructions but without inclusion of an RNase H digest.

Quantitative PCR was performed using TaqMan® Gene Expression Assays on an ABI PRISM® 7900HT Sequence Detection System according to the manufacturer's recommendations (Applied Biosystems, CA, USA). All assays were performed in triplicate.

The used primers and probes crossed exon boundaries or were within the Affymetrix Genechip® probe sequence of interest. Two house-keeping genes were included as endogenous controls: beta-2-microglobulin (B2M; Assay Hs99999907_m1) and hypoxanthinephosphoribosyl transferase (HPRT; Assay Hs99999909_m1).

All runs included a calibrator sample (MVP™ total RNA from human adult lung; Stratagene, CA, USA) and a standard curve. Universal Human Reference total RNA (Stratagene, CA, USA) was used as template for PTPRF standard curves. All samples were measured in triplicate.

Relative quantification was performed using the $-\Delta Ct$ method.

Results

As reported previously, Affymetrix Genechip® gene expression profiles were determined for 102 patients included in this study. Among these patients, qRT-PCR results were obtained for 75 (table 4). The demographics and clinical characteristics of the patients with qRT-PCR results were similar to those of the entire population (n=264) and of the patients with Genechip® gene expression profiles available.

TABLE 4

Baseline characteristics: patients with qRT-PCR analyses (n = 75)

| Characteristic | |
|---|---|
| Age (median, range) | 62 (39-85) |
| Gender; n (%) | |
| Male | 19 (25) |
| Female | 56 (75) |
| ECOG performance status; n (%) | |
| 0 | 7 (9) |
| 1 | 45 (60) |
| 2 | 23 (31) |
| Histology; n (%) | |
| Adenocarcinoma | 27 (36) |
| Squamous-cell carcinoma | 34 (45) |
| Large-cell carcinoma | 2 (3) |
| Other | 12 (16) |
| Disease stage; n (%) | |
| IIIB | 22 (29) |
| IV | 53 (71) |
| Number of prior chemotherapy regimens; n (%) | |
| 0 | 19 (25) |
| 1 | 36 (48) |

TABLE 4-continued

Baseline characteristics: patients with qRT-PCR analyses (n = 75)

| Characteristic | |
|---|---|
| ≥2 | 20 (27) |
| Ethnicity; n (%) | |
| Caucasian | 51 (68) |
| Asian | 24 (32) |
| Smoking history; n (%) | |
| Never | 12 (16) |
| Current | 24 (32) |
| Former | 39 (52) |

Of the 75 patients with qRT-PCR results, 4 (5%) had partial response (PR), 23 (31%) had SD, 39 (52%) had PD, and 9 (12%) were not evaluable. These results were very similar to those observed in the entire study population (n=264).

Figure 3A:
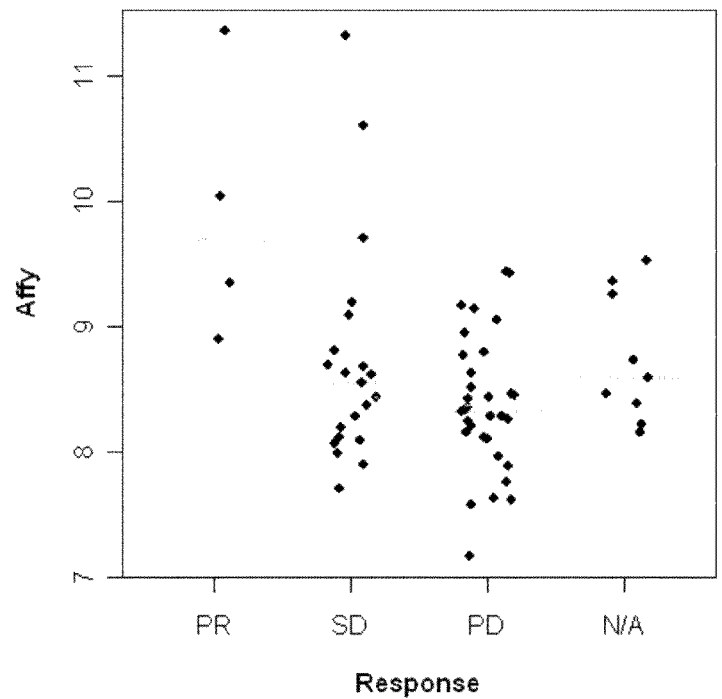
FIG. 3a shows PTPRF expression levels versus clinical outcome for Genechip® profiling.
Figure 3B:
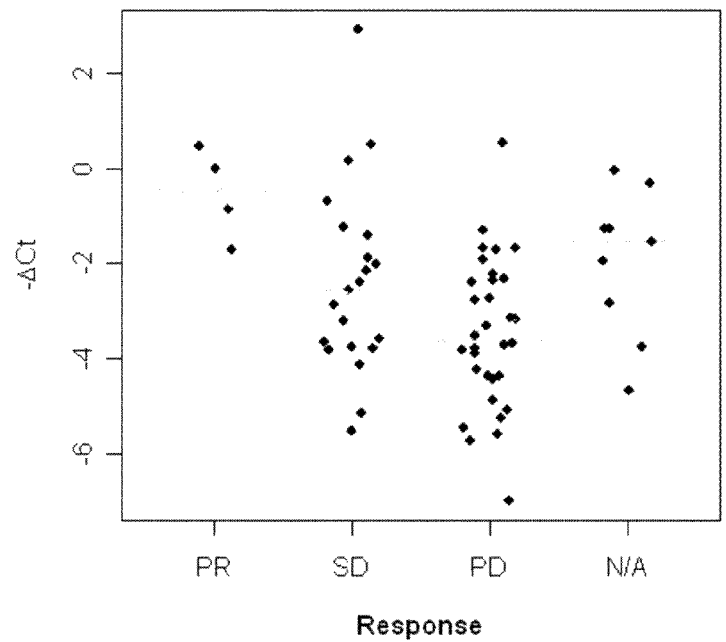
FIG. 3b shows PTPRF expression levels versus clinical outcome for qRT-PCR.

FIG. 3 shows relative mRNA levels for PTPRF in individual patients, as assessed by Affymetrix Genechip® profiling and qRT-PCR. FIG. 3a shows expression levels versus clinical outcome for Genechip® profiling and FIG. 3b shows expression levels to qRT-PCR.

Figure 3C:
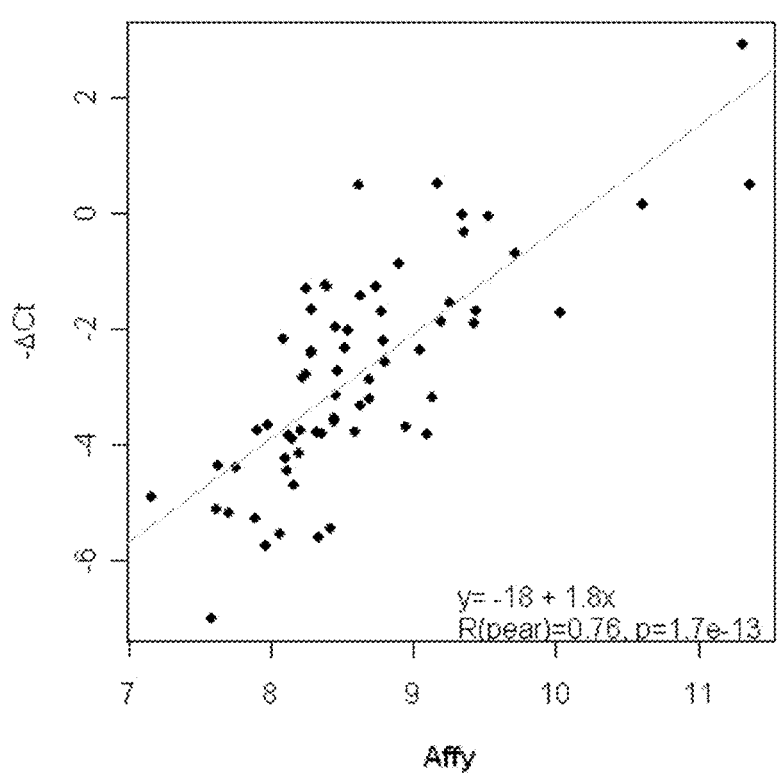
FIG. 3c shows the correlation between Genechip® and qRT-PCR measurements for PTPRF.

There was a good correlation between Genechip® and qRT-PCR measurements of the PTPRF mRNA transcript (FIG. 3c; pearson's p=0.76, p<0.01). As observed with Genechip® profiling, PTPRF mRNA levels assessed using qRT-PCR appeared to correlate with response to erlotinib, with higher levels being observed in responders compared with non-responders.

Discussion

By analyzing tissue samples with high-density oligonucleotide microarray technology, and applying statistical modeling to the data, we have been able to identify genes whose expression levels may be predictive of patients deriving a clinical benefit from treatment with erlotinib.

A composite criterion (defined above) was applied. It resulted in PTPRF as predictive marker for EGFR inhibitor treatment.

The PTPRF gene, located on chromosome 1p34, encodes a protein member of the protein tyrosine phosphatase (PTP) family. It possesses an extracellular region, a single transmembrane region, and two tandem intracytoplasmic catalytic domains, and thus represents a receptor-type PTP. The extracellular region contains three Ig-like domains, and nine non-Ig like domains, similar to that of neural-cell adhesion molecule.

In this study, PTPRF was found to be relatively up regulated in patients deriving a clinical benefit from treatment with erlotinib. This finding can be interpreted in the context of published reports demonstrating the potential role of this gene in different important mechanisms of tumourigenesis.

Firstly, it was clearly established that EGFR is a substrate of PTPRF. In a detailed investigation, the interaction between EGFR and PTPRF was further characterized and shown to be complex and tightly controlled. These observations have lead us to postulate that PTPRF plays an important and direct role in controlling downstream signaling from EGFR receptor. In another line of evidence, PTPRF was observed to have a tumour suppressor activity, acting through an inhibitory effect on cell migration and possibly induction of apoptosis. The mechanism by which PTPRF controls the cell migration process was further elicited. Two studies have shown that this protein functions by a complex interaction with the E-cadherin complex, mediated by a direct regulation of the activity of beta-catenin.

Direct interaction with EGFR and a well characterized tumour suppressor activity are two prominent features making PTPRF a particularly compelling marker of response to erlotinib.

The invention claimed is:

1. A method of treating a human NSCLC patient that will derive clinical benefit from treatment with erlotinib, said method comprising:
  (i) assaying, in vitro, the level of protein tyrosine phosphatase receptor type F (PTPRF) RNA in a tumor sample of a human NSCLC patient,
  (ii) comparing the level of PTPRF RNA in the tumor sample to a value representative of the level of PTPRF RNA in tumors of a population of human NSCLC patients that derive no clinical benefit from erlotinib treatment,
  (iii) determining that the level of PTPRF RNA in the tumor sample of the human NSCLC patient is higher than the value representative of the level of PTPRF RNA in tumors of a population of human NSCLC patients that derive no clinical benefit from erlotinib treatment and that the human NSCLC patient will derive clinical benefit from erlotinib treatment; and
  (iv) administering a therapeutically effective amount of erlotinib to the human NSCLC patient.

* * * * *

SEQUENCE LISTING

```
<160> NUMBER OF SEQ ID NOS: 2

<210> SEQ ID NO 1
<211> LENGTH: 7733
<212> TYPE: DNA
<213> ORGANISM: Homo sapiens

<400> SEQUENCE: 1
cgggagcggc gggagcggtg gcggcggcag aggcggcggc tccagcttcg gctccggctc      60
gggctcgggc tccggctccg gctccggctc cggctccagc tcgggtggcg gtggcggag     120 cgggaccagg tggaggcggc ggcggcagag gagtgggagc agcggcccta gcggcttgcg    180
gggggacatg cggaccgacg gcccctggat aggcggaagg agtggaggcc ctggtgcccg    240
gcccttggtg ctgagtatcc agcaagagtg accgggtga agaagcaaag actcggttga    300
ttgtcctggg ctgtggctgg ctgtggagct agagccctgg atggcccctg agccagcccc    360
agggaggacg atggtgcccc ttgtgcctgc actggtgatg cttggtttgg tggcaggcgc    420
ccatggtgac agcaaacctg tcttcattaa agtccctgag gaccagactg ggctgtcagg    480
aggggtagcc tccttcgtgt gccaagctac aggagaaccc aagccgcgca tcacatggat    540
gaagaagggg aagaaagtca gctcccagcg cttcgaggtc attgagtttg atgatgggc    600 agggtcagtg cttcggatcc agccattgcg ggtgcagcga gatgaagcca tctatgagtg    660
tacagctact aacagcctgg gtgagatcaa cactagtgcc aagctctcag tgctcgaaga    720
```

```
ggaacagctg ccccctgggt tcccttccat cgacatgggg cctcagctga aggtggtgga    780
gaaggcacgc acagccacca tgctatgtgc cgcaggcgga atccagacc  ctgagatttc    840
ttggttcaag gacttccttc ctgtagaccc tgccacgagc aacggccgca tcaagcagct    900
gcgttcaggt gccttgcaga tagagagcag tgaggaatcc gaccaaggca agtacgagtg    960
tgtggcgacc aactcggcag gcacacgtta ctcagcccct gcgaacctgt atgtgcgagt   1020
gcgccgcgtg gctcctcgtt tctccatccc tcccagcagc caggaggtga tgccaggcgg   1080
cagcgtgaac ctgacatgcg tggcagtggg tgcacccatg ccctacgtga agtggatgat   1140
gggggccgag gagctcacca aggaggatga gatgccagtt ggccgcaacg tcctggagct   1200
cagcaatgtc gtacgctctg ccaactacac ctgtgtggcc atctcctcgc tgggcatgat   1260
cgaggccaca gcccaggtca cagtgaaagc tcttccaaag cctccgattg atcttgtggt   1320
gacagagaca actgccacca gtgtcaccct cacctgggac tctgggaact cggagcctgt   1380
aacctactat ggcatccagt accgcgcagc gggcacggag ggccccttc  aggaggtgga   1440
tggtgtggcc accaccgct  acagcattgg cggcctcagc cctttctcgg aatatgcctt   1500
ccgcgtgctg gcggtgaaca gcatcgggcg agggccgccc agcgaggcag tgcgggcacg   1560
cacgggagaa caggcgccct ccagcccacc gcgccgcgtg caggcacgca tgctgagcgc   1620
cagcaccatg ctggtgcagt gggagcctcc cgaggagccc aacggcctgg tgcggggata   1680
ccgcgtctac tatactccgg actcccgccg cccccccgaac gcctggcaca agcacaacac   1740
cgacgcgggg ctcctcacga ccgtgggcag cctgctgcct ggcatcacct acagcctgcg   1800
cgtgcttgcc ttcaccgccg tgggcgatgg ccctcccagc ccaccatcc  aggtcaagac   1860
gcagcaggga gtgcctgccc agcccgcgga cttccaggcc gaggtggagt cggacaccag   1920
gatccagctc tcgtggctgc tgcccccctca ggagcggatc atcatgtatg aactggtgta   1980
ctgggcggca gaggacgaag accaacagca caaggtgacc ttcgacccaa cctcctccta   2040
cacactagag gacctgaagc ctgacacact ctaccgcttc cagctggctg cacgctcgga   2100
tatgggggtg ggcgtcttca cccccaccat tgaggcccgc acagcccagt ccacccctc    2160
cgcccctccc cagaaggtga tgtgtgtgag catgggctcc accacggtcc gggtaagttg   2220
ggtcccgccg cctgccgaca gccgcaacgg cgttatcacc cagtactccg tggcctacga   2280
ggcggtggac ggcgaggacc gcgggcggca tgtggtggat ggcatcagcc gtgagcactc   2340
cagctgggac ctggtgggcc tggagaagtg gacggagtac cgggtgtggg tgcgggcaca   2400
cacagacgtg ggcccggcc  cgagagcag  cccggtgctg gtgcgcaccg atgaggacgt   2460
gcccagcggg cctccgcgga aggtggaggt ggagccactg aactccactg ctgtgcatgt   2520
ctactggaag ctgcctgtcc ccagcaagca gcatggccag atccgcggct accaggtcac   2580
ctacgtgcgg ctggagaatg cgagccccg  tggactcccc atcatccaag acgtcatgct   2640
agccgaggcc cagtggcggc cagaggagtc cgaggactat gaaaccacta tcagcggcct   2700
gacccccgag accacctact ccgttactgt tgctgcctat accaccaagg gggatggtgc   2760
ccgcagcaag cccaaaattg tcactacaac aggtgcagtc ccaggccggc ccaccatgat   2820
gatcagcacc acggccatga acactgcgct gctccagtgg cacccaccca aggaactgcc   2880
tggcgagctg ctgggctacc ggctgcagta ctgccgggcc gacgaggcgc ggcccaacac   2940
catagatttc ggcaaggatg accagcactt cacagtcacc ggcctgcaca aggggaccac   3000
ctacatcttc cggcttgctg ccaagaaccg ggctggcttg ggtgaggagt tcagaaggga   3060
gatcaggacc cccgaggacc tgcccagcgg cttcccccaa aacctgcatg tgacaggact   3120
```

```
gaccacgtct accacagaac tggcctggga cccgccagtg ctggcggaga ggaacgggcg   3180
catcatcagc tacaccgtgg tgttccgaga catcaacagc caacaggagc tgcagaacat   3240
cacgacagac acccgcttta cccttactgg cctcaagcca gacaccactt acgacatcaa   3300
ggtccgcgca tggaccagca aaggctctgg cccactcagc cccagcatcc agtcccggac   3360
catgccggtg gagcaagtgt ttgccaagaa cttccgggtg gcggctgcaa tgaagacgtc   3420
tgtgctgctc agctgggagg ttcccgactc ctataagtca gctgtgccct ttaagattct   3480
gtacaatggg cagagtgtgg aggtggacgg gcactcgatg cggaagctga tcgcagacct   3540
gcagcccaac acagagtact cgtttgtgct gatgaaccgt ggcagcagcg cagggggcct   3600
gcagcacctg gtgtccatcc gcacagcccc cgacctcctg cctcacaagc cgctgcctgc   3660
ctctgcctac atagaggacg gccgcttcga tctctccatg ccccatgtgc aagacccctc   3720
gcttgtcagg tggttctaca ttgttgtggt gcccattgac cgtgtgggcg ggagcatgct   3780
gacgccaagg tggagcacac ccgaggaact ggagctggac gagcttctag aagccatcga   3840
gcaaggcgga gaggagcagc ggcggcggcg gcggcaggca gaacgtctga agccatatgt   3900
ggctgctcaa ctggatgtgc tcccggagac ctttaccttg ggggacaaga gaactaccg   3960
gggcttctac aaccggcccc tgtctccgga cttgagctac cagtgctttg tgcttgcctc   4020
cttgaaggaa cccatggacc agaagcgcta tgcctccagc ccctactcgg atgagatcgt   4080
ggtccaggtg acaccagccc agcagcagga ggagccggag atgctgtggg tgacgggtcc   4140
cgtgctggca gtcatcctca tcatcctcat tgtcatcgcc atcctcttgt tcaaaaggaa   4200
aaggacccac tctccgtcct ctaaggatga gcagtcgatc ggactgaagg actccttgct   4260
ggcccactcc tctgaccctg tggagatgcg gaggctcaac taccagaccc caggtatgcg   4320
agaccaccca cccatcccca tcaccgacct ggcggacaac atcgagcgcc tcaaagccaa   4380
cgatggcctc aagttctccc aggagtatga gtccatcgac cctggacagc agttcacgtg   4440
ggagaattca aacctggagg tgaacaagcc caagaaccgc tatgcgaatg tcatcgccta   4500
cgaccactct cgagtcatcc ttacctctat cgatggcgtc cccggagtg actacatcaa   4560
tgccaactac atcgatggct accgcaagca gaatgcctac atcgccacgc agggccccct   4620
gcccgagacc atgggtgatt tctgaggat ggtgtgggaa cagcgcacgg ccactgtggt   4680
catgatgaca cggctggagg agaagtcccg ggtaaaatgt gatcagtact ggccagcccg   4740
tggcaccgag acctgtggcc ttattcaggt gaccctgttg gacacagtgg agctggccac   4800
atacactgtg cgcaccttcg cactccacaa gagtggctcc agtgagaagc gcgagctgcg   4860
tcagtttcag ttcatggcct ggccagacca tggagttcct gagtacccaa ctcccatcct   4920
ggccttccta cgacgggtca aggcctgcaa ccccctagac gcaggcccca tggtggtgca   4980
ctgcagcgcg ggcgtgggcc gcaccggctg cttcatcgtg attgatgcca tgttggagcg   5040
gatgaagcac gagaagacgg tggacatcta tggccacgtg acctgcatgc gatcacagag   5100
gaactacatg gtgcagacgg aggaccagta cgtgttcatc catgaggcgc tgctggaggc   5160
tgccacgtgc ggccacacag aggtgcctgc ccgcaacctg tatgcccaca tccagaagct   5220
gggccaagtg cctccagggg agagtgtgac cgccatggag ctcgagttca gttgctggc   5280
cagctccaag gcccacacgt cccgcttcat cagcgccaac ctgccctgca caagttcaa   5340
gaaccggctg gtgaacatca tgccctacga attgaccgt gtgtgtctgc agcccatccg   5400
tggtgtggag ggctctgact acatcaatgc cagcttcctg gatggttata gacagcagaa   5460
```

```
ggcctacata gctacacagg ggcctctggc agagagcacc gaggacttct ggcgcatgct    5520
atgggagcac aattccacca tcatcgtcat gctgaccaag cttcgggaga tgggcaggga    5580
gaaatgccac cagtactggc cagcagagcg ctctgctcgc taccagtact ttgttgttga    5640
cccgatggct gagtacaaca tgccccagta tatcctgcgt gagttcaagg tcacggatgc    5700
ccgggatggg cagtcaagga caatccggca gttccagttc acagactggc cagagcaggg    5760
cgtgcccaag acaggcgagg gattcattga cttcatcggg caggtgcata agaccaagga    5820
gcagtttgga caggatgggc ctatcacggt gcactgcagt gctggcgtgg gccgcaccgg    5880
ggtgttcatc actctgagca tcgtcctgga gcgcatgcgc tacgagggcg tggtcgacat    5940
gtttcagacc gtgaagaccc tgcgtacaca gcgtcctgcc atggtgcaga cagaggacca    6000
gtatcagctg tgctaccgtg cggcctgga gtacctcggc agctttgacc actatgcaac    6060
gtaactaccg ctcccctctc ctccgccacc cccgccgtgg ggctccggag gggacccagc    6120
tcctctgagc cataccgacc atcgtccagc cctcctacgc agatgctgtc actggcagag    6180
cacagcccac ggggatcaca gcgtttcagg aacgttgcca caccaatcag agagcctaga    6240
acatccctgg gcaagtggat ggcccagcag gcaggcactg tggcccttct gtccaccaga    6300
cccacctgga gcccgcttca agctctctgt tgcgctcccg catttctcat gcttcttctc    6360
atggggtggg gttggggcaa agcctccttt ttaatacatt aagtgggta gactgaggga    6420 ttttagcctc ttccctctga tttttccttt cgcgaatccg tatctgcaga atgggccact    6480
gtaggggttg gggtttattt tgtttttgttt ttttttttct tgagttcact ttggatcctt    6540
attttgtatg acttctgctg aaggacagaa cattgccttc ctcgtgcaga gctgggctg    6600 ccagcctgag cggaggctcg gccgtgggcc gggaggcagt gctgatccgg ctgctcctcc    6660
agcccttcag acgagatcct gtttcagcta aatgcaggga aactcaatgt ttttttaagt    6720
tttgttttcc cttaaagcc ttttttagg ccacattgac agtggtggc ggggagaaga    6780 tagggaacac tcatccctgg tcgtctatcc cagtgtgtgt ttaacattca cagcccagaa    6840
ccacagatgt gtctgggaga gcctggcaag gcattcctca tcaccatcgt gtttgcaaag    6900
gttaaaacaa aaacaaaaaa ccacaaaaat aaaaacaaa aaaaacaaaa aacccaagaa    6960 aaaaaaaag agtcagccct tggcttctgc ttcaaaccct caagagggga agcaactccg    7020
tgtgcctggg gttcccgagg gagctgctgg ctgacctggg cccacagagc ctggcttggg    7080
tccccagcat tgcagtatgg tgtggtgttt gtaggctgtg gggtctggct gtgtggccaa    7140
ggtgaatagc acaggttagg gtgtgtgcca caccccatgc acctcagggc caagcgggg    7200 cgtggctggc ctttcaggtc caggccagtg ggcctggtag cacatgtctg tcctcagagc    7260
aggggccaga tgatttttcct ccctggtttg cagctgtttt caaagccccc gataatcgct    7320 ctttttccact ccaagatgcc ctcataaacc aatgtggcaa gactactgga cttctatcaa    7380
tggtactcta atcagtcctt attatcccag cttgctgagg ggcagggaga gcgcctcttc    7440
ctctgggcag cgctatctag ataggtaagt gggggcgggg aagggtgcat agctgtttta    7500
gctgagggac gtggtgccga cgtccccaaa cctagctagg ctaagtcaag atcaacattc    7560
cagggttggt aatgttggat gatgaaacat tcatttttac cttgtggatg ctagtgctgt    7620
agagttcact gttgtacaca gtctgttttc tatttgttaa gaaaaactac agcatcattg    7680
cataattctt gatggtaata aatttgaata atcagatttc ttacaaacca gga    7733

<210> SEQ ID NO 2
<211> LENGTH: 7706
```

<212> TYPE: DNA
<213> ORGANISM: Homo sapiens

<400> SEQUENCE: 2

```
cgggagcggc gggagcggtg gcggcggcag aggcggcggc tccagcttcg gctccggctc      60
gggctcgggc tccggctccg gctccggctc cggctccagc tcgggtggcg gtggcgggag     120
cgggaccagg tggaggcggc ggcggcagag gagtgggagc agcggcccta gcggcttgcg     180
ggggacatg cggaccgacg gcccctggat aggcggaagg agtggaggcc ctggtgcccg      240
gcccttggtg ctgagtatcc agcaagagtg accggggtga agaagcaaag actcggttga     300
ttgtcctggg ctgtggctgg ctgtggagct agagccctgg atggcccctg agccagcccc     360
agggaggacg atggtgcccc ttgtgcctgc actggtgatg cttggtttgg tggcaggcgc     420
ccatggtgac agcaaacctg tcttcattaa agtccctgag accagactg gctgtcagg      480
aggggtagcc tccttcgtgt gccaagctac aggagaaccc aagccgcgca tcacatggat     540
gaagaagggg aagaaagtca gctcccagcg cttcgaggtc attgagtttg atgatggggc     600
agggtcagtg cttcggatcc agccattgcg ggtgcagcga gatgaagcca tctatgagtg     660
tacagctact aacagcctgg gtgagatcaa cactagtgcc aagctctcag tgctcgaaga     720
ggaacagctg ccccctgggt tcccttccat cgacatgggg cctcagctga aggtggtgga     780
gaaggcacgc acagccacca tgctatgtgc cgcaggcgga aatccagacc ctgagatttc     840
ttggttcaag gacttccttc tgtagaccc tgccacgagc aacggccgca tcaagcagct     900
gcgttcaggt gccttgcaga tagagagcag tgaggaatcc gaccaaggca gtacgagtg     960
tgtggcgacc aactcggcag gcacacgtta ctcagcccct gcgaacctgt atgtgcgagt    1020
gcgccgcgtg gctcctcgtt tctccatccc tcccagcagc caggaggtga tgccaggcgg    1080
cagcgtgaac ctgacatgcg tggcagtggg tgcacccatg ccctacgtga agtggatgat    1140
gggggccgag gagctcacca aggaggatga gatgccagtt ggccgcaacg tcctggagct    1200
cagcaatgtc gtacgctctg ccaactacac ctgtgtggcc atctcctcgc tgggcatgat    1260
cgaggccaca gcccaggtca cagtgaaagc tcttccaaag cctccgattg atcttgtggt    1320
gacagagaca actgccacca gtgtcaccct cacctgggac tctgggaact cggagcctgt    1380
aacctactat ggcatccagt accgcgcagc gggcacggag ggccccttc aggaggtgga    1440
tggtgtggcc accaccgct acagcattgg cggcctcagc cctttctcgg aatatgcctt    1500
ccgcgtgctg gcggtgaaca gcatcgggcg agggccgccc agcgaggcag tgcgggcacg    1560
cacgggagaa caggcgccct ccagcccacc gcgccgcgtg caggcacgca tgctgagcgc    1620
cagcaccatg ctggtgcagt gggagcctcc cgaggagccc aacggcctgg tgcgggata    1680
ccgcgtctac tatactccgg actcccgccg ccccccgaac gcctggcaca gcacaacac    1740
cgacgcgggg ctcctcacga ccgtgggcag cctgctgcct ggcatcacct acagcctgcg    1800
cgtgcttgcc ttcaccgccg tgggcgatgg ccctcccagc ccaccatcc aggtcaagac    1860
gcagcaggga gtgcctgccc agcccgcgga cttccaggcc gaggtggagt cggacaccag    1920
gatccagctc tcgtggctgc tgccccctca ggagcggatc atcatgtatg aactggtgta    1980
ctgggcggca gaggacgaag accaacagca caaggtgacc ttcgacccaa cctcctccta    2040
cacactagag gacctgaagc ctgacacact ctaccgcttc cagctggctg cacgctcgga    2100
tatgggggtg ggcgtcttca cccccaccat tgaggcccgc acagcccagt ccaccccctc    2160
cgccccctccc cagaaggtga tgtgtgtgag catgggctcc accacggtcc gggtaagttg    2220
```

-continued

```
ggtcccgccg cctgccgaca gccgcaacgg cgttatcacc cagtactccg tggcctacga    2280
ggcggtggac ggcgaggacc gcgggcggca tgtggtggat ggcatcagcc gtgagcactc    2340
cagctgggac ctggtgggcc tggagaagtg gacggagtac cgggtgtggg tgcgggcaca    2400
cacagacgtg ggccccggcc ccgagagcag cccggtgctg gtgcgcaccg atgaggacgt    2460
gcccagcggg cctccgcgga aggtggaggt ggagccactg aactccactg ctgtgcatgt    2520
ctactggaag ctgcctgtcc ccagcaagca gcatggccag atccgcggct accaggtcac    2580
ctacgtgcgg ctggagaatg cgagccccg tggactcccc atcatccaag acgtcatgct    2640
agccgaggcc caggaaaacca ctatcagcgg cctgaccccg agaccacct actccgttac    2700 tgttgctgcc tataccacca aggggatgg tgcccgcagc aagcccaaaa ttgtcactac    2760
aacaggtgca gtcccaggcc ggcccaccat gatgatcagc accacggcca tgaacactgc    2820
gctgctccag tggcacccac ccaaggaact gcctggcgag ctgctgggct accggctgca    2880
gtactgccgg gccgacgagg cgcggcccaa caccatagat ttcggcaagg atgaccagca    2940
cttcacagtc accggcctgc acaagggac cacctacatc ttccggcttg ctgccaagaa    3000
ccgggctggc ttgggtgagg agttcgagaa ggagatcagg accccgagg acctgcccag    3060 cggcttcccc caaaacctgc atgtgacagg actgaccacg tctaccacag aactggcctg    3120
ggacccgcca gtgctggcgg agaggaacgg gcgcatcatc agctacaccg tggtgttccg    3180
agacatcaac agccaacagg agctgcagaa catcacgaca gacacccgct ttacccttac    3240
tggcctcaag ccagacacca cttacgacat caaggtccgc gcatggacca gcaaaggctc    3300
tggcccactc agcccagca tccagtcccg gaccatgccg gtggagcaag tgtttgccaa    3360
gaacttccgg gtggcggctg caatgaagac gtctgtgctg ctcagctggg aggttcccga    3420
ctcctataag tcagctgtgc cctttaagat tctgtacaat gggcagagtg tggaggtgga    3480
cgggcactcg atgcggaagc tgatcgcaga cctgcagccc aacacagagt actcgtttgt    3540
gctgatgaac cgtggcagca gcgcaggggg cctgcagcac ctggtgtcca tccgcacagc    3600
ccccgacctc ctgcctcaca gccgctgcc tgcctctgcc tacatagagg acggccgctt    3660
cgatctctcc atgccccatg tgcaagaccc ctcgcttgtc aggtggttct acattgttgt    3720
ggtgcccatt gaccgtgtgg gcgggagcat gctgacgcca aggtggagca cccgagga    3780 actggagctg gacgagcttc tagaagccat cgagcaaggc ggagaggagc agcggcggcg    3840
gcggcggcag gcagaacgtc tgaagccata tgtggctgct caactggatg tgctcccgga    3900
gaccttaccc ttgggggaca agaagaacta ccggggcttc tacaaccggc ccctgtctcc    3960
ggacttgagc taccagtgct tgtgcttgc ctccttgaag gaacccatgg accagaagcg    4020
ctatgcctcc agcccctact cggatgagat cgtggtccag gtgacaccag cccagcagca    4080
ggaggagccg gagatgctgt gggtgacggg tccgtgctg gcagtcatcc tcatcatcct    4140
cattgtcatc gccatcctct tgttcaaaag gaaaaggacc cactctccgt cctctaagga    4200
tgagcagtcg atcggactga aggactcctt gctggcccac tcctctgacc ctgtggagat    4260
gcggaggctc aactaccaga ccccaggtat gcgagaccac ccacccatcc ccatcaccga    4320
cctggcggac aacatcgagc gcctcaaagc caacgatggc ctcaagttct cccaggagta    4380
tgagtccatc gaccctggac agcagttcac gtgggagaat tcaaacctgg aggtgaacaa    4440
gcccaagaac cgctatgcga atgtcatcgc ctacgaccac tctcgagtca tccttacctc    4500
tatcgatggc gtccccggga gtgactacat caatgccaac tacatcgatg ctaccgcaa    4560 gcagaatgcc tacatcgcca cgcagggccc cctgcccgag accatgggtg atttctggag    4620
```

```
gatggtgtgg gaacagcgca cggccactgt ggtcatgatg acacggctgg aggagaagtc    4680
ccgggtaaaa tgtgatcagt actggccagc ccgtggcacc gagacctgtg gccttattca    4740
ggtgaccctg ttggacacag tggagctggc cacatacact gtgcgcacct tcgcactcca    4800
caagagtggc tccagtgaga agcgcgagct gcgtcagttt cagttcatgg cctggccaga    4860
ccatggagtt cctgagtacc caactcccat cctggccttc ctacgacggg tcaaggcctg    4920 caaccccta gacgcagggc ccatggtggt gcactgcagc gcgggcgtgg gccgcaccgg    4980
ctgcttcatc gtgattgatg ccatgttgga gcggatgaag cacgagaaga cggtggacat    5040
ctatggccac gtgacctgca tgcgatcaca gaggaactac atggtgcaga cggaggacca    5100
gtacgtgttc atccatgagg cgctgctgga ggctgccacg tgcggccaca cagaggtgcc    5160
tgcccgcaac ctgtatgccc acatccagaa gctgggccaa gtgcctccag gggagagtgt    5220
gaccgccatg gagctcgagt tcaagttgct ggccagctcc aaggcccaca cgtcccgctt    5280
catcagcgcc aacctgcccct gcaacaagtt caagaaccgg ctggtgaaca tcatgcccta    5340
cgaattgacc cgtgtgtgtc tgcagcccat ccgtggtgtg gagggctctg actacatcaa    5400
tgccagcttc ctggatggtt atagacagca gaaggcctac atagctacac aggggcctct    5460
ggcagagagc accgaggact tctggcgcat gctatgggag cacaattcca ccatcatcgt    5520
catgctgacc aagcttcggg agatgggcag ggagaaatgc caccagtact ggccagcaga    5580
gcgctctgct cgctaccagt actttgttgt tgacccgatg gctgagtaca acatgcccca    5640
gtatatcctg cgtgagttca aggtcacgga tgcccgggat gggcagtcaa ggacaatccg    5700
gcagttccag ttcacagact ggccagagca gggcgtgccc aagacaggcg agggattcat    5760
tgacttcatc gggcaggtgc ataagaccaa ggagcagttt ggacaggatg gcctatcac     5820 ggtgcactgc agtgctggcg tgggccgcac cggggtgttc atcactctga gcatcgtcct    5880
ggagcgcatg cgctacgagg gcgtggtcga catgtttcag accgtgaaga ccctgcgtac    5940
acagcgtcct gccatggtgc agacagagga ccagtatcag ctgtgctacc gtgcggccct    6000
ggagtacctc ggcagctttg accactatgc aacgtaacta ccgctcccct ctcctccgcc    6060 accccgccg tggggctccg gaggggaccc agctcctctg agccataccg accatcgtcc     6120
agccctccta cgcagatgct gtcactggca gagcacagcc cacggggatc acagcgtttc    6180
aggaacgttg ccacaccaat cagagagcct agaacatccc tggcaagtg gatggcccag     6240 caggcaggca ctgtggccct tctgtccacc agacccacct ggagcccgct tcaagctctc    6300
tgttgcgctc ccgcatttct catgcttctt ctcatggggt ggggttgggg caaagcctcc    6360
tttttaatac attaagtggg gtagactgag ggattttagc ctcttccctc tgatttttcc    6420
tttcgcgaat ccgtatctgc agaatgggcc actgtagggg ttggggttta ttttgttttg    6480
tttttttttt tcttgagttc actttggatc cttattttgt atgacttctg ctgaaggaca    6540
gaacattgcc ttcctcgtgc agagctgggg ctgccagcct gagcggaggc tcggccgtgg    6600
gccgggaggc agtgctgatc cggctgctcc tccagcccct cagacgagat cctgtttcag    6660
ctaaatgcag ggaaactcaa tgtttttttta agttttgttt ccccttaaa gccttttttt     6720 aggccacatt gacagtggtg ggcggggaga agatagggaa cactcatccc tggtcgtcta    6780
tcccagtgtg tgtttaacat tcacagccca gaaccacaga tgtgtctggg agagcctggc    6840
aaggcattcc tcatcaccat cgtgtttgca aaggttaaaa caaaaacaaa aaccacaaa     6900 aataaaaaac aaaaaaaaca aaaacccaa gaaaaaaaaa aagagtcagc ccttggcttc    6960
```

```
tgcttcaaac cctcaagagg ggaagcaact ccgtgtgcct ggggttcccg agggagctgc        7020
tggctgacct gggcccacag agcctggctt tggtccccag cattgcagta tggtgtggtg        7080
tttgtaggct gtggggtctg gctgtgtggc caaggtgaat agcacaggtt agggtgtgtg        7140
ccacacccca tgcacctcag ggccaagcgg gggcgtggct ggcctttcag gtccaggcca        7200
gtgggcctgg tagcacatgt ctgtcctcag agcaggggcc agatgatttt cctccctggt        7260
ttgcagctgt tttcaaagcc cccgataatc gctcttttcc actccaagat gccctcataa        7320
accaatgtgg caagactact ggacttctat caatggtact ctaatcagtc cttattatcc        7380
cagcttgctg aggggcaggg agagcgcctc ttcctctggg cagcgctatc tagataggta        7440
agtgggggcg gggaagggtg catagctgtt ttagctgagg gacgtggtgc cgacgtcccc        7500
aaacctagct aggctaagtc aagatcaaca ttccagggtt ggtaatgttg gatgatgaaa        7560
cattcatttt taccttgtgg atgctagtgc tgtagagttc actgttgtac acagtctgtt        7620
ttctatttgt taagaaaaac tacagcatca ttgcataatt cttgatggta ataaatttga        7680
ataatcagat ttcttacaaa ccagga                                              7706
```